United States Patent [19]

Poindexter

[11] Patent Number: 5,240,469
[45] Date of Patent: Aug. 31, 1993

[54] ANTIFOULANT COMPOSITION COMPRISING AN ACRYLATE ESTER CONTAINING $C_4$-$C_{22}$ ALCOHOL ESTERS AND AMINO ALCOHOL ESTERS AND PHENYLENE DIAMINE

[75] Inventor: Michael K. Poindexter, Sugar Land, Tex.

[73] Assignee: Nalco Chemical Company, Naperville, Ill.

[21] Appl. No.: 874,790

[22] Filed: Apr. 27, 1992

[51] Int. Cl.[5] .................................................. C10L 1/22
[52] U.S. Cl. .................................... 44/392; 44/430; 203/6; 203/8
[58] Field of Search .............. 44/412, 430, 432, 392; 203/6, 8

[56] References Cited

U.S. PATENT DOCUMENTS

| 2,734,808 | 2/1956 | Biswell | 44/431 |
| 2,974,025 | 3/1961 | Ertelt et al. | 44/412 |
| 3,336,124 | 8/1967 | Dunworth | 44/412 |
| 3,363,999 | 1/1968 | Gary | 44/412 |
| 3,674,651 | 7/1972 | Otsuki et al. | 203/8 |
| 4,240,804 | 12/1980 | Shields | 44/432 |
| 4,365,081 | 12/1982 | Shimizu et al. | 203/8 |
| 4,744,881 | 5/1988 | Reid | 44/412 |
| 5,023,372 | 6/1991 | Roling | 562/598 |
| 5,110,997 | 5/1992 | Dickakian | 203/6 |

Primary Examiner—Margaret Medley
Attorney, Agent, or Firm—Robert A. Miller; John G. Premo; Joseph B. Barrett

[57] ABSTRACT

A method for preventing fouling of ethylene dichloride distillation units which comprises treating the feed to such units with a fouling preventing amount of a composition comprising:

| INGREDIENTS | WEIGHT % |
|---|---|
| a) An oil soluble polymethacrylate ester which contains from between .1-25 mole % of amino alcohol ester groups with the balance of the alcohol radical of the ester group containing from $C_4$-$C_{22}$ carbon atoms, | 2-15 |
| b) a phenylene diamine compound having the formula: 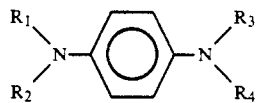 wherein $R_1$, $R_2$, $R_3$, and $R_4$ are the same or different and are hydrogen, $C_1$-$C_{20}$ alkyl, $C_1$-$C_{20}$ aryl, $C_1$-$C_{20}$ alkaryl or $C_1$-$C_{20}$ aralkyl, with the proviso that at least one of $R_1$, $R_2$, $R_3$ or $R_4$ is hydrogen, and | 20-40 |
| c) a heavy aromatic solvent | Balance |

4 Claims, No Drawings

ANTIFOULANT COMPOSITION COMPRISING AN ACRYLATE ESTER CONTAINING $C_4$-$C_{22}$ ALCOHOL ESTERS AND AMINO ALCOHOL ESTERS AND PHENYLENE DIAMINE

DESCRIPTION OF THE INVENTION

Fouling in ethylene dichloride distillation units can be minimized and prevented by utilizing as a treating agent an oil soluble polymethacrylate or polyacrylate ester which contains amino alcohol ester groups in combination with certain phenylenediamines.

General Field of the Invention

Prevention of fouling in ethylene dichloride distillation units.

INTRODUCTION

Vinyl chloride monomer (VCM) is obtained by cracking pure (usually >99.5 wt %) 1,2-dichloroethane (also called ethylene dichloride, EDC) at 425° to 550° C. Ethylene dichloride is in turn generally produced from two different metal catalyzed reactions—the direct chlorination of ethylene and an oxychlorination reaction involving ethylene, an oxygen containing gas (usually air or oxygen), and HCl (the latter is a by-product of ethylene dichloride pyrolysis). The overall production of vinyl chloride is balanced with respect to HCl since there is ultimately no net consumption or production of HCl. Pure ethylene dichloride is needed for the furnaces since the direct chlorination of ethylene yields other unwanted chlorinated products (and the oxychlorination reaction likewise yields unwanted oxygenates/chlorides) which unfortunately do not produce desired vinyl chloride on pyrolysis and can even inhibit the cracking of ethylene dichloride to vinyl chloride. Furthermore, certain impurities not removed from vinyl chloride can upon polymerization yield poly(vinyl chloride) with undesirable properties.

Materials from the direct chlorination unit often contain not only chlorinated products, but also iron complexes; the iron typically comes from the catalyst (e.g. ferric chloride or tetrachloroferrate salts) used in the reaction or from corrosion of the equipment used in the process. These unwanted species, i.e. extraneous organic chloride/oxygenates and iron complexes, are typically removed through a series of aqueous washings and distillation columns. Columns are used to concentrate and remove the tars (i.e. heavies) formed either during the chlorination step or downstream of the reactors. Tars are generally high boiling polychlorinated by-products with poorly defined compositions. Material lighter than ethylene dichloride (b.p. 83° C.) is also removed through fractionation. After prolonged usage, both types of columns eventually foul due to the accumulation of non-volatile by-products.

Some of the by-products are likely due to unwanted oxidation (e.g. chloral and other oxygenated by-products are known to form). Oxygen is frequently an impurity in chlorine, and oxygen is also used in the oxychlorination process. Infrared analysis of non-volatile components from a heavy ends removal column has revealed that carbonyl moieties do indeed exist.

It is not uncommon for these units to foul within periods of time as short as a few days. If it were possible, by the use of additives, to increase the time before fouling caused shut downs for cleaning a valuable contribution to the art would be made. Not only would running length of the unit be increased, but there would be a reduction in waste and lower potential exposure to those who clean the unit.

THE INVENTION

In accordance with the invention there is provided a method for preventing fouling of ethylene dichloride distillation units which comprises treating the feed to such units with a fouling preventing amount of a composition comprising:

| INGREDIENTS | WEIGHT % |
|---|---|
| a) An oil soluble polymethacrylate ester which contains from .1-25 mole % of amino alcohol groups; | 2-15 |
| b) a phenylene diamine compound having the formula: 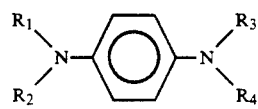 wherein $R_1$, $R_2$, $R_3$, and $R_4$ are the same or different and are hydrogen, $C_1$-$C_{20}$ alkyl, $C_1$-$C_{20}$ aryl, $C_1$-$C_{20}$ alkaryl or $C_1$-$C_{20}$ aralkyl, with the proviso that at least one of $R_1$, $R_2$, $R_3$, or $R_4$ is hydrogen; and, | 20-40 |
| c) a heavy aromatic solvent. | Balance |

The compositions of the type described above are capable of preventing fouling when fed at dosages, based on actives, ranging between as little as 15 ppm up to as high as 500 ppm. Typically, dosages within the range of 25-100 ppm give excellent results with respect to preventing fouling and extending the time in which these units can operate before it is necessary to remove or clean the fouling deposits formed therein.

THE OIL SOLUBLE ACRYLATE ESTERS

The oil-soluble acrylate esters useful in this invention are oil-soluble polyacrylate esters and more particularly esters of either polyacrylic or polymethacrylic acid with polymethacrylic acid esters being preferred. As indicated, the esters are oil-soluble. To impart this characteristic to these materials, it is necessary that they contain hydrophobic groupings. This is achieved by using as the esterifying alcohol one or more paraffinic alcohols containing at least 4 carbon atoms. Typically, best results are achieved when esters are mixed esters prepared from alcohols having alkyl groups of varying lengths, such as alcohols which contain 4-22 carbon atoms. Typical of these alcohols are mixed butyl, lauryl, oleyl stearyl, and other mixed higher alkyl groups which are commonly found in fatty acids derived from animal fats and vegetable oils. Saturated alkyl groups are preferred.

Another important characteristic of these acrylate and methacrylate copolymer esters is that they contain between 0.1-25 mole percent acrylate or methacrylate amino alcohol esters. In a preferred embodiment of the invention, the amount of acrylate amino alcohol ester contained in the acrylate oil soluble copolymer is between about 0.5-10 mole percent and most preferably 1-5 mole percent. Commercially, these products are a mixed composition that cannot be identified with exactitude. Illustrative of the amino alcohols that can be used in the preparation of the oil-soluble acrylate and methacrylate esters described above are the alkanol amines, such as ethanol amine, propanol amine, and the like. In a preferred embodiment of the invention, the alkanol amine is a tertiary amine. A typical alcohol of this class is 2-dimethylaminoethanol. The acrylate and methacrylate copolymer esters typically will have an average molecular weight in the range of from 150,000 up to 1,000,000. Typical molecular weight ranges of the preferred materials are between about 400,000 to 700,000.

The acrylate and methacrylate esters of this invention are typically prepared by esterifying the selected vinyl carboxylic acid with a $C_4$-$C_{22}$ alcohol, amino alcohol, or mixtures thereof, recovering the esterified vinyl monomers and then polymerizing the resultant esters to form the polymers useful in this invention. Alternatively, a polyacrylic or methacrylic acid may be esterified with the $C_4$-$C_{22}$ alcohol and amino alcohol.

Materials useful in this invention are available commercially. A preferred material for use in my invention is TC-8103 available from Texaco Company, Houston, Tex.

The functionality of the polymers of this invention appears to be as a dispersant for gums and the like formed during the reaction process. The amino alcohol ester groups appear to provide a polar site where the dispersant anchors or attaches to the gum or resin foulant. As such, any oil soluble polymer having dispersant properties and polar sites may function as anti-foulants in this invention, it not being necessary to have a hydrophobic group attached to the amino group if the polymer is sufficiently oil soluble.

THE PHENYLENEDIAMINES

Phenylenediamines that may be used in the invention include phenylenediamines having at least one N-H bond. It is thought that o-phenylenediamine or derivatives thereof having at least one N—H bond are suitable in accordance with the instant invention.

The preferred phenylenediamines are the p-phenylenediamines having the structure

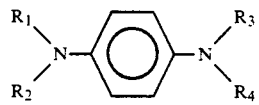

wherein R1, R2, R3, and R4 are the same or different and are hydrogen, alkyl, aryl, alkaryl, or aralkyl groups with the proviso that at least one of R1, R2, R3, or R4 is hydrogen. More preferable, the alkyl, aryl, alkaryl, and aralkyl groups have one to about twenty carbon atoms. The alkyl, aryl, alkaryl, and aralkyl groups may be straight or branched-chain groups.

A comprehensive list of such phenylenediamines is set forth in Col. 2 and 3 of U.S. Pat. No. 5,023,372. This particular disclosure, as well as the entire disclosure of US 5,023,372 is incorporated herein by reference.

A particularly effective phenylenediamine composition is a blend of phenylenediamines which consists of:
A. N-(1,3-Dimethylbutyl)-N'-phenyl-p-phenylenediamine.
B. N-(1,4-Dimethylpentyl)-N'-phenyl-p-phenylenediamine.

THE HEAVY AROMATIC SOLVENT

Solvents of this type are well known and are produced from the refining of various types of petroleum fractions. They usually contain a substantial number of substituted aromatic compounds. The solvent selected for use in the invention should have a relatively high boiling point, e.g. in excess of the boiling point of the light ends that are removed during the distillation and purification of ethylene dichloride.

EVALUATION OF THE INVENTION

The following composition and its ingredients were evaluated as a fouling preventative for ethylene dichloride distillation units.

| Composition 1 | | |
|---|---|---|
| Component | | Weight % |
| 1. A polymethacrylate Consisting of: | | 25 |
| | A. 35-50% solvent-dewaxed heavy paraffinic petroleum distillates. | |
| | B. 35-50% Methacrylic acid, copolymer-Texaco TC-8103 esterified with: | |
| | 1. A mixture of butyl, lauryl and stearyl alcohols, | |
| | 2. .1-25 mole % dimethylaminoethyl alcohol, and | |
| | C. 11-20% solvent-refined heavy paraffinic petroleum distillates | |
| 2. Phenylenediamine Consisting of: | | 30 |
| | A. 30.7% N-(1,3-Dimethylbutyl)-N'-phenyl-p-phenylenediamine | |
| | B. 61.3% N-(1,4-Dimethylpentyl)-N'-phenyl-p-phenylenediamine | |
| 3. Heavy aromatic Naphtha solvent | | 45 |

Bottom samples from two heavy ends removal columns (hereafter called column 1 and column 2 where 1 is before 2 in the process) were laboratory tested whit regards to their oxidative stability and how likely their existing gums (i.e. tars or heavies), which were isolated from streams, could be stabilized with the aid of dispersants. These tests were used to gain an initial understanding of product performance and to make a product recommendation.

EXAMPLE 1

Several different analyses and evaluations were performed on streams taken from the bottom of both columns. As seen in Table 1, column 1 contained a relatively high level of foulant while column 2 contained noticeably less (see values with the superscript a). Table 1 also demonstrates the oxidative susceptibility of the two streams. Heating under 100 psig of nitrogen with a trace of oxygen or 100 psig of oxygen alone gave substantially more foulant than the existent gum yields. Weights were taken after all the volatile components had been evaporated.

TABLE 1

| Sample Source | Atmosphere | Grams - Foulant/25mL of Bottoms |
|---|---|---|
| Column 1 Bottoms | — | 4.076[a] |
| | trace $O_2$ | 6.187[b] |
| | $O_2$ | 9.364[b] |
| Column 2 Bottoms | — | 0.038[a] |
| | trace $O_2$ | 0.302[b] |

TABLE 1-continued

| Sample Source | Atmosphere | Grams - Foulant/25mL of Bottoms |
|---|---|---|
| | $O_2$ | $0.658^b$ |

[a]Values indicate existent gum levels for the two streams. Determined by removing volatiles.
[b]Samples were heated for 3 hours at 100° C.

Addition of various additives to the above degradation tests showed different levels of performance. The best products were phenylenediamines, PDAs. In particular a mixture of N-(1,3-dimethylbutyl)-N'-phenyl-p-phenylenediamine and N-(1,4-dimethylpentyl)-N'-phenyl-p-phenylenediamine, Component 2 of Composition 1, performed extremely well. N,N'-bis-(1,4-dimethylpentyl)-p-phenylenediamine also worked quite well.

EXAMPLE 2

Using conditions identical to Table 1, except heating for two hours instead of three hours, it was found that the phenylene diamine mixture was superior at inhibiting fouling than other additive classes, see Table 2. The product showed performance on both streams, but was clearly superior on material from column 2.

TABLE $2^a$

| Sample | Dosage (ppm) | Grams-Foulant/25 mL | % Reduction[b] |
|---|---|---|---|
| Column 1 | 0 | 2.306 | 0 |
| | 100 | 2.054 | 11 |
| | 200 | 1.920 | 17 |
| Column 2 | 0 | 0.261 | 0 |
| | 100 | 0.036 | 86 |
| | 200 | 0.039 | 85 |

[a]Results for using phenylene diamine mixture.
[b]Percent reduction=[(grams of gum formed with no additive - grams of gum formed at a given dosage) / grams of gum formed with no additive] × 100%.

EXAMPLE 3

Dispersant testing was undertaken to determine whether certain additives could suspend foulant (i.e. the heavies) in a "poor" solvent. The procedure involves evaporating the volatiles from the column samples and then redissolving the heavies into the original solvent stream or another solvent of choice. In essence, a concentrated foulant or gum solution is obtained in which the exact concentration is known. The gum solution is then added to a poor solvent (in this case hexane) which is known to precipitate the heavies. An activity relationship is sought where an additive (in most cases a type of dispersant) when added beforehand to the poor solvent demonstrates the ability to solubilize the heavies under conditions which the heavies are known to flocculate. The dispersant in effect modifies how the foulant behaves with itself and its environment.

Gum solutions composed of material from both columns were tested with a variety of dispersants. A polymethacrylate composed of butyl, lauryl, stearyl, and dimethylaminoethyl esters of methacrylic acid with an average molecular weight of 450,000-610,000 was superior in preventing tar precipitation; lab results are given in Table 3. Values range from 0-100% (in which 100% represents total dispersion).

TABLE 3

| PERCENT DISPERSION OF FOULANTS USING POLYMETHACRYLATE DISPERSANT | | | |
|---|---|---|---|
| DISPERSANT | COLUMN $1^a$ | COLUMN $1^b$ | COLUMN $2^a$ |
| 0 | 0 | 0 | 0 |
| 10 | 5 | 9 | 5 |
| 50 | 29 | 85 | 100 |
| 100 | 51 | 88 | 100 |
| 500 | 91 | 88 | 100 |

[a]Foulant dissolved in stream from column 2.
[b]Foulant dissolved in toluene (done as a comparison).

EXAMPLE 4

In an extended plant trial, using the columns from which the samples used in Examples 1-3 were obtained, the performance of both column 1 and column 2 was significantly increased by adding Composition 1 at 200 ppm to the feed of both columns. Prior to addition of the additives, column 1, a distillation tower, ran for three days before needing a clean-out while column 2 reboiler ran for five days before it was rendered ineffective. Under identical process conditions, addition of the two additives resulted in a subsequent 49 day column 1 run and a 63 day column 2 reboiler run.

While I have described my invention in relationship to ethylene dichloride units, the method and composition of this invention may find applicability in the prevention of fouling during the processing of other hydrocarbons, particularly other halogenated hydrocarbons and particularly chlorinated hydrocarbons.

Having thus described my invention, I claim:

1. An antifoulant composition consisting essentially of:

a) 2-15 weight percent of an oil soluble polyacrylate or polymethacrylate ester which contains from between, with the balance of the alcohol radical of the ester group containing from $C_4$-$C_{22}$ carbon atoms, 1-25 mole % of aliphatic amino alcohol ester groups with the amino alcohol radical of the ester group containing from 2 to 3 carbon atoms;

b) 20-40 weight percent of at least one phenylene diamine compound having the formula

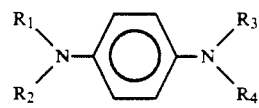

wherein R1, R2, R3, and R4 are the same or different and are hydrogen, C1-C20 alkyl, C1-C20 aryl, C1-C20 alkaryl or C1-C20 aralkyl, with the proviso that at least one of R1, R2, R3 or R4 is hydrogen, and, c) the balance is a heavy aromatic solvent.

2. The composition of claim 1 wherein the amino alcohol ester groups are 2-dimethylaminoethyl alcohol groups.

3. The composition of claim 1 wherein the oil soluble polyacrylate ester is polymethacrylic acid esterified with a mixture of butyl, lauryl, and stearyl alcohols and 1-10 mole % of 2-dimethylaminoethyl alcohol.

4. The composition of claim 1 wherein the phenylene diamine is a mixture of phenylenediamines consisting of N-(1,3-dimethylbutyl)-N'-phenyl-p-phenylenediamine and N-(1,4-dimethylpentyl)-N'phenyl-p-phenylenediamine.

* * * * *

UNITED STATES PATENT AND TRADEMARK OFFICE
CERTIFICATE OF CORRECTION

PATENT NO. : 5,240,469
DATED : August 31, 1993
INVENTOR(S) : MICHAEL K. POINDEXTER It is certified that error appears in the above-identified patent and that said Letters Patent is hereby corrected as shown below:

CLAIM 1, COLUMN 6, LINE 37, 38, 39 DELETE

[WITH THE BALANCE OF THE ALCOHOL RADICAL OF THE ESTER GROUP CONTAINING FROM C4-C22 CARBON ATOMS]

CLAIM 1, COLUMN 6, LINE 42 ADD UNDERLINE

WITH THE BALANCE OF THE ALCOHOL RADICAL OF THE ESTER GROUP CONTAINING FROM C4-C22 CARBON ATOMS

Signed and Sealed this

Twelfth Day of April, 1994

Attest:

BRUCE LEHMAN

*Attesting Officer*    *Commissioner of Patents and Trademarks*